(12) United States Patent
Becke et al.

(10) Patent No.: US 6,403,735 B1
(45) Date of Patent: Jun. 11, 2002

(54) METHOD FOR PRODUCING FULVENE METAL COMPLEXES

(75) Inventors: Sigurd Becke, Rösrath; Rüdiger Beckhaus, Oldenburg; Jürgen Heinrichs, Aachen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/530,812

(22) PCT Filed: Oct. 28, 1998

(86) PCT No.: PCT/EP98/06821

§ 371 (c)(1),
(2), (4) Date: May 5, 2000

(87) PCT Pub. No.: WO99/24445

PCT Pub. Date: May 20, 1999

(30) Foreign Application Priority Data

Nov. 7, 1997 (DE) .......................... 197 49 293
Dec. 19, 1997 (DE) .......................... 197 56 742

(51) Int. Cl.⁷ .............................. B01J 31/00; C08F 4/64
(52) U.S. Cl. ................... 526/160; 526/941; 556/53; 502/102; 502/104; 502/117; 502/152
(58) Field of Search ................ 502/102, 104, 502/117, 152; 526/160, 941; 556/53

(56) References Cited

U.S. PATENT DOCUMENTS

| | | | |
|---|---|---|---|
| 4,542,199 A | 9/1985 | Kaminsky et al. | 526/160 |
| 4,808,561 A | 2/1989 | Welborn, Jr. | 502/104 |
| 4,892,851 A | 1/1990 | Ewen et al. | 502/104 |
| 4,912,075 A | 3/1990 | Chang | 502/107 |
| 4,914,253 A | 4/1990 | Chang | 585/523 |
| 5,008,228 A | 4/1991 | Chang | 502/111 |
| 5,145,819 A | 9/1992 | Winter et al. | 502/117 |
| 5,276,208 A | 1/1994 | Winter et al. | 556/53 |
| 5,324,800 A | 6/1994 | Welborn, Jr. et al. | 526/160 |
| 5,334,677 A | 8/1994 | Razavi et al. | 526/114 |
| 5,580,939 A | 12/1996 | Ewen et al. | 526/127 |
| 5,633,394 A | 5/1997 | Welborn, Jr. et al. | 556/11 |
| 6,054,405 A | * 4/2000 | Wenzel | 502/104 |

FOREIGN PATENT DOCUMENTS

| | | |
|---|---|---|
| EP | 277003 | 3/1988 |
| EP | 277004 | 3/1988 |

OTHER PUBLICATIONS

Fandos et al., Organometallics, 1991, 10, 1637–1639.*
Schock et al., Organometallics, 1987, 6, 232–241.*
Journal of Organometallic Chemistry, vol. 311, (month unavailable) 1986, pp 111–123, XP002095813, F. Edelmann, et al "Übergangsmetall–Fulven–Komplexe XXIX. Benzofulven–Komplexe des Chroms und Eisens".
Journal of the American Chemical Society, Bd. 110, (month unavailable) 1988, Seiten 7701–7715, XP002095814, in der Anmeldung erwähnt siehe das ganze Dokument, L. E. Schock et al, "Organometallic Thermochemistry. Metal Hydrocarbyl, Hydride, Halide, Carbonyl, Amide, and Alkoxide Bond Enthalpy Relationships and Their Implications in Pentamethylcyclopentadienyl and Cyclopentadienyl Complexes of Zirconium and Hafnium".
J. Am. Chem. Soc., (month unavailable), 1997, 119, pp 5132–5143, Yimin Sun, et al Intramolecular Ion–Ion Interactions in Zwitterionic Metallocene Olefin Polymerization Catalysts Derived from "Tucked–In" Catalyst Precursors and the Highly Electrophilic Boranes $XB(C_6F_5)_2$ (X=H, $C_6F_5$).
JACS, Feb. 23, 1972, 94, pp 1219–1237, J. E. Bercaw et al, "Titanocene as an Intermediate in Reactions Involving Molecular Hydrogen and Nitrogen".
Organometallics (month unavailable) 1997, 16, pp 842–857, Li Jia et al, "Catonic Metallocene Polymerization Catalysts Based on Tetrakis(pentafluorophenyl)borate and Its Derivatives. Probing the Limits of Anion "Noncorrdination" via a Synthetic, Solution Dynamic, Structural and Catalytic Olefin Polymerization Study".
J. Chem. Soc., (month unavailable), 1960, pp 1321–1324, E. W. Abel et al, Some π–Cyclopentadienyl–molybdenum and —tungsten Carbonyls.
J. Chem. Soc., Dalton Trans. (month unavailable), 1985, pp 2037–2049, Judith A Bandy et al, "Synthesis, Structure, and Bonding of Fulvene Complexes of Titanium, Molybdenum, and Tungsten".
J. Org. Chem, vol 49, No. 11, Jun. 1, 1984, K. J. Stone et al, "An Exceptionally Simple and Efficient Method for the Preparation of a Wide Variety of Fulvenes".

* cited by examiner

Primary Examiner—David W. Wu
Assistant Examiner—Caixia Lu
(74) Attorney, Agent, or Firm—Joseph C. Gil; Noland J. Cheung (57) ABSTRACT

The present invention relates to a process for the preparation of fulvene complexes, and their use as catalysts for the polymerization of unsaturated compounds.

8 Claims, 1 Drawing Sheet

FIGURE 1

METHOD FOR PRODUCING FULVENE METAL COMPLEXES

This application is 371 of international application No. PCT EP98/06821, filed Oct. 28, 1998.

FIELD OF THE INVENTION

The present invention relates to a process for the preparation of fulvene-metal complexes, new fulvene-metal complexes and their use as catalysts for the polymerization of unsaturated compounds, in particular for the polymerization and copolymerization of olefins and/or dienes.

BACKGROUND OF THE INVENTION

Metal complexes with cyclopentadienyl ligands have been the subject of intense investigation since the discovery of ferrocene. The use of cyclopentadienyl-metal complexes, in particular the use of metallocene complexes as a mixture with activating cocatalysts, preferably alumoxanes, for the polymerization of olefins and diolefins has been known for a long time (e.g. EP-A 69 951, 129 368, 351 392, 485 821, 485 823). Metallocenes have proved to be highly active, specific catalysts in the polymerization of olefins. A large number of new metallocene catalysts and metallocene catalyst systems for the polymerization of olefinic compounds have therefore been developed in recent years in order to increase the activity, selectivity, control of the microstructure, molecular weights and molecular weight distribution.

Comparatively little is known of metal complexes with fulvene ligands.

J. Am. Chem. Soc. 1997, 119, 5132 describes zwitterionic olefin polymerization catalysts which are formed in the reaction of specific ($\eta^6$-2,3,4,5-tetramethylcyclopentadienyl-1-methylene) ($\eta^5$-pentamethylcyclopentadienyl)zirconium compounds with tris(pentafluorophenyl)boron or bis(pentafluorophenyl)borane. The synthesis of the ($\eta^6$-2,3,4,5-tetramethylcyclopentadienyl-1-methylene)($\eta^5$-pentamethylcyclopentadienyl)zirconium compound is very expensive, it first being necessary to prepare a metallocene with pentamethylcyclopentadienyl ligands, which is decomposed by a thermolysis reaction in the last synthesis stage. Such thermolysis reactions are described in the literature.

According to Bercaw et al., JACS (1972), 94, 1219, the fulvene complex ($\eta^6$-2,3,4,5-tetramethylcyclopentadienyl-1-methylene)($\eta^5$-pentamethylcyclopentadienyl)titanium-methyl is formed by thermolysis of bis($\eta^5$-pentamethylcyclopentadienyl)titanium-dimethyl. T. J. Marks et al., JACS (1988), 110, 7701 describe the thermolysis of pentamethylcyclopentadienyl complexes of zirconium and hafnium. The fulvene complex ($\eta^6$-2,3,4,5-tetramethylcyclopentadienyl-1-methylene)$\eta^5$-pentamethylcyclopentadienyl)zirconium-phenyl is formed by thermolysis of bis($\eta^5$-pentamethylcyclopentadienyl)zirconium-diphenyl.

The preparation of fulvene complexes by the thermal process is limited to a few structural variants. The thermal process does not always lead to uniform products.

G. Wilkinson et al. in J. Chem. Soc. 1960, 1321–1324 describe the reaction of 6,6-dialkylfulvenes with chromium-hexacarbonyl or molybdenum-hexacarbonyl. However, cyclopentadienyl-metal complexes are obtained instead of the fulvene-metal complexes.

In J. Chem. Soc. Dalton Trans. (1985), 2037, M. L. H. Green et al. report the synthesis of bis($\eta^6$-6,6-diphenylfulvene)titanium by reaction of bis(toluene)titanium with 6,6-diphenylfulvene. However, the bis(toluene)titanium must be prepared by involved and expensive metal atom vaporization techniques. For this, metallic titanium is vaporized and condensed in a matrix together with gaseous toluene. The yield of bis(toluene)titanium is very low. The bis(toluene)titanium is therefore accessible to only a limited extent.

SUMMARY OF THE INVENTION

There was therefore the object of discovering an improved process for the preparation of fulvene-metal complexes which avoids the disadvantages mentioned.

It has now been found, surprisingly, that fulvene-metal complexes can be prepared by reaction of a fulvene compound with a suitable transition metal complex in the presence of a reducing agent.

DETAILED DESCRIPTION OF THE INVENTION

The present invention thus provides a process for the preparation of fulvene-metal complexes of the formula (Ia)

(Ia)

or of the formula (Ib)

(Ib)

wherein
  M is a metal from group IIIb, IVb, Vb or VIb or the lanthanides or the actinides. of the periodic table of the elements according to IUPAC,
  A denotes an anionic ligand optionally with one or more bridges,
  X denotes a hydrogen atom, a $C_1$- to $C_{10}$-alkyl group, a C- to $C_{10}$-alkoxy group, a $C_6$- to $C_{10}$-aryl group, a $C_6$- to $C_{10}$-aryloxy group, a $C_2$- to $C_{10}$-alkenyl group, a $C_7$- to $C_{40}$-arylalkyl group, a $C_7$-to $C_{40}$-alkylaryl group, a $C_8$- to $C_{40}$-arylalkenyl group, a silyl group substituted by $C_1$- to $C_{10}$-hydrocarbon radicals, a halogen atom or an amide of the formula $NR^7{}_2$,
  L denotes a neutral ligand,
  $R^1$, $R^2$, $R^3$, $R^4$, $R^5$, $R^6$ are identical or different and represent hydrogen, halogen, a cyano group, a $C_1$- to $C_{20}$-alkyl group, a $C_1$- to $C_{10}$-fluoroalkyl group, a $C_6$- to $C_{10}$-fluoromyl group, a $C_1$- to $C_{10}$-alkoxy group, a $C_6$- to $C_{20}$-aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a $C_2$- to $C_{10}$-alkenyl group, a silyl group substituted by $C_1$–$C_{10}$-hydrocarbon radicals, a sulfide group substituted by a $C_1$–$C_{10}$-hydrocarbon radical or an amino group which is optionally substituted by $C_1$–$C_{20}$-hydrocarbon radicals, or $R^1$, $R^2$, $R^3$, $R^4$, $R^5$, $R^6$, in each case together with the atoms connecting them, form one or more aliphatic or aromatic ring systems, which can contain one or more heteroatoms (O, N, S) and 5 to 10 carbon atoms, $R^7$ represents hydrogen, a $C_1$- to $C_{20}$-alkyl group, a $C_6$- to $C_{20}$-aryl group, a $C_7$- to $C_{40}$-arylalkyl group, a $C_7$- to $C_{40}$-alkylaryl group, a silyl group substituted by $C_1$–$C_{10}$-hydrocarbon radicals or an amino group which is optionally substituted by $C_1$–$C_{20}$-hydrocarbon radicals, m, p represent the numbers 0, 1, 2, 3 or 4, which result from the valency and the bonding state of M, and k represents the number 1, 2 or 3, and the sum of k+m+p is 1 to 5, depending on the oxidation level of M, and n is a number from 0 to 10, by reaction of a transition metal compound of the formula (IIa) or (IIb)

(IIa)

or

(IIb)

wherein

A, X, L, M, m, s and n have the abovementioned meaning and s is 2, 3, 4, 5 or 6 and s is >p, with a fulvene compound of the formula (III)

(III)

wherein $R^1$, $R^2$, $R^3$, $R^4$, $R^5$ and $R^6$ have the abovementioned meaning, in the presence of a reducing agent.

The preparation of the fulvene-metal complexes of the formula (I) is to be illustrated by the following equation:

The reaction can be carried out in a single reaction step, i.e. in a one-pot reaction, the sequence of addition of the individual reaction components not being fixed. The reaction can also be carried out in separate reaction steps. For example, transition metal compounds of the formula (IIa) or (IIb) can first be brought into contact with a reducing agent and reacted with fulvene compounds of the formula (III) in a separate reaction step. It is furthermore preferable first to add the transition metal compound (IIa) or (IIb) to the fulvene compound (III) and then to add the reducing agent.

Examples of suitable reducing agents are alkali metals, alkaline earth metals, aluminium, zinc, alloys of the alkali metals, such as e.g. sodium-potassium alloys or sodium amalgam, alloys of the alkaline earth metals, and metal hydrides. Examples of metal hydrides are lithium hydride, sodium hydride, magnesium hydride, aluminium hydride, lithium aluminium hydride and sodium borohydride. Specific examples of reducing agents are sodium naphthalenide, potassium graphite, lithium-alkyls, magnesium-butadiene, magnesium-anthracene, trialkylaluminium compounds and Grignard reagents. Preferred reducing agents are alkali metals or alkaline earth metals, $C_1$–$C_6$-alkyllithium, tri-$C_1$–$C_6$-alkylaluminium compounds and Grignard reagents. Preferred reducing agents are lithium, magnesium, n-butyllithium and triethylaluminium and triisobutylaluminium. Instead of the reducing agents mentioned, it is also possible to carry out an electrochemical reduction.

The process for the preparation of the fulvene-metal complexes of the formula (I) is carried out in a suitable reaction medium at temperatures of −100 to +250° C., preferably −78 to +130° C., particularly preferably −10 to +120° C.

Examples of possible suitable reaction media are aliphatic or aromatic hydrocarbons, halogenated hydrocarbons, ethers and cyclic ethers. Examples of these are unbranched aliphatic hydrocarbons, such as butane, pentane, hexane, heptane and octane, branched aliphatic hydrocarbons, such as isobutane, isopentane and isohexane, cyclic aliphatic hydrocarbons, such as cyclohexane and methylcyclohexane, aromatic hydrocarbons, such as benzene, toluene and xylene, and ethers, such as dialkyl ethers, dimethoxyethane and tetrahydrofuran. Mixtures of various solvents are also suitable.

The fulvene-metal complexes of the formula (I) are prepared and handled with the exclusion of air and water under inert gas conditions (inert gas technique). Examples of inert gases are nitrogen or argon. The Schlenk technique generally conventional for organometallic substances is suitable, for example, as an inert gas technique.

The falvene-metal complexes of the formula (I) can be isolated or employed directly for further reactions. If isolation is necessary, the by-products formed can be removed by conventional methods of purification, e.g. by filtration. Alternatively, the desired products can also be extracted with a solvent, If necessary, a purification operation, e.g. recrystallization, can be carried out.

Possible transition metal complexes of the formula (IIa) or (IIb) are, in particular, those in which M is a metal from the group consisting of titanium, zirconium, hafnium, vanadium, niobium, tantalum and chromium, A is a pyrazolate of the formula $N_2C_3R^8_3$ where $R^8$ represents hydrogen or a $C_1$–$C_{10}$-alkyl group or a $C_6$–$C_{10}$-aryl group,
a pyrazolylborate of the formula $R^7B(N_2C_3R^8_3)_3$,
an alcoholate or phenolate of the formula $OR^7$,
a siloxane of the formula $OSiR^7_3$,
a thiolate of the formula $SR^7$,
an acetylacetonate of the formula $(R^7CO)_2CR^7$,
a diimine of the formula $(R^7N=CR^7)_2$,
an amidinate of the formula $R^7C(NR^7_2)_2$,
a cyclooctatetraenyl of the formula $C_8H_qR^7_{8-q}$ where q is 0, 1, 2, 3, 4, 5, 6 or 7,
a cyclopentadienyl of the formula $C_5H_qR^7_{5-q}$ where q is 0, 1, 2, 3, 4 or 5,
an indenyl of the formula $C_9H_{7-r}R^7_r$ where r is 0, 1, 2, 3, 4, 5, 6 or 7,
a fluorenyl of the formula $C_{13}H_{9-s}R^7_s$ where s is 0, 1, 2, 3, 4, 5, 6, 7, 8 or 9 or
a $C_1$- to $C_{30}$-alkyl radical, a $C_6$- to $C_{10}$-aryl radical or a $C_7$- to $C_{40}$-alkylaryl radical and L, X, $R^7$, m, s and n have the abovementioned meaning.

Especially preferred transition metal complexes of the formula (IIa) or (IIb) are those in which M represents titanium, zirconium or hafnium, A represents bis(trimethylsilyl)amide, dimethylamide, diethylamide, diisopropylamide, 2,6-di-tert-butyl-4-methylphenolate, cyclooctatetraenyl, cyclopentadienyl, methylcyclopentadienyl, benzylcyclopentadienyl, n-propylcyclopentadienyl, n-butylcyclopentadienyl, iso-butylcyclopentadienyl, t-butylcyclopentadienyl, cyclopentylcyclopentadienyl, octadecylcyclopentadienyl, 1,2-dimethylcyclopentadienyl, 1,3-dimethylcyclopentadienyl, 1,3-diisopropylcyclopentadienyl, 1,3-di-t-butylcyclopentadienyl, 1-ethyl-2-methylcyclopentadienyl, 1-isopropyl-3-methylcyclopentadienyl, 1-(n-butyl)-3-methylcyclopentadienyl, 1-(t-butyl)-3-methylcyclopentadienyl, pentamethylcyclopentadienyl, 1,2,3,4-tetramethylcyclopentadienyl, 1,2,4-trimethylcyclopentadienyl, 1,2,4-triisopropylcyclopentadienyl, 1,2,4-tri-(t-butyl)-cyclopentadienyl, indenyl, tetrahydroindenyl, 2-methylindenyl, 4,7-dimethylindenyl, 2-methyl-4,5-benzoindenyl, 2-methyl-4-phenylindenyl, fluorenyl or 9-methylfluorenyl,

X denotes fluorine or chlorine and

L, m, s and n have the abovementioned meaning.

Possible fulvene compounds are, in particular, those of the formula (III) in which

$R^1$ to $R_6$ represents a $C_1$–$C_{30}$-alkyl group, a $C_6$–$C_{10}$-aryl group or a $C_7$–$C_{40}$-alkylaryl group, in particular hydrogen, methyl, trifluoromethyl, ethyl, n-propyl, isopropyl, n-butyl, isobutyl, tert-butyl, phenyl, pentafluorophenyl, methylphenyl, cyclohexyl or benzyl.

Preferred compounds of the formula (III) are fulvene compounds of the formula (IV)

(IV)

or fulvene compounds of the formula (V)

(V)

wherein $R^1$, $R^2$, $R^3$ and $R^4$ have the abovementioned meaning.

Particularly preferred compounds of the formula (III) are 6-cyclohexylfulvene, 6-isopropylfulvene, 6-tert-butylfulvene, 6-phenylfulvene, 6-(dimethylamino)fulvene, 6,6-bis(dimethylamino)fulvene, 6,6-dimethylfulvene, 6,6-bis(trifluoromethyl)-fulvene, 6,6-diphenylfulvene, 6,6-bis(pentafluorophenyl)fulvene, 6,6-pentamethylenefulvene, 6,6-tetramethylenefulvene, 6,6-trimethylenefuilvene, 2-(2,4-cyclopentadien-1-ylidene)-1,3-dithiolane, 5-benzylidene-1,2,3-triphenyl-1,3-cyclopentadiene, 1,2,3,4-tetramethylfulvene, 1,2,3,4-tetraphenylfulvene, 2,3-dimethylfulvene, 2,3-diisopropylfulvene, 2,3-diphenylfulvene, 1,4-dimethyl-2,3-diphenylfulvene and 1,4-diethyl-2,3-diphenylfulvene.

The synthesis of the fulvene compounds of the formula (III), (IV) and (V) can be carried out, for example, in accordance with the method of J. Org. Chem., Vol. 49, No. 11 (1984), 1849.

The formula (I) given for the fulvene-metal complexes is to be regarded as a formal illustration of the bonding circumstances. The bonding circumstances in the metal complexes depend, inter alia, on the central atom, on the oxidation level and on the substituents of the fulvene ligand.

Figure 1:
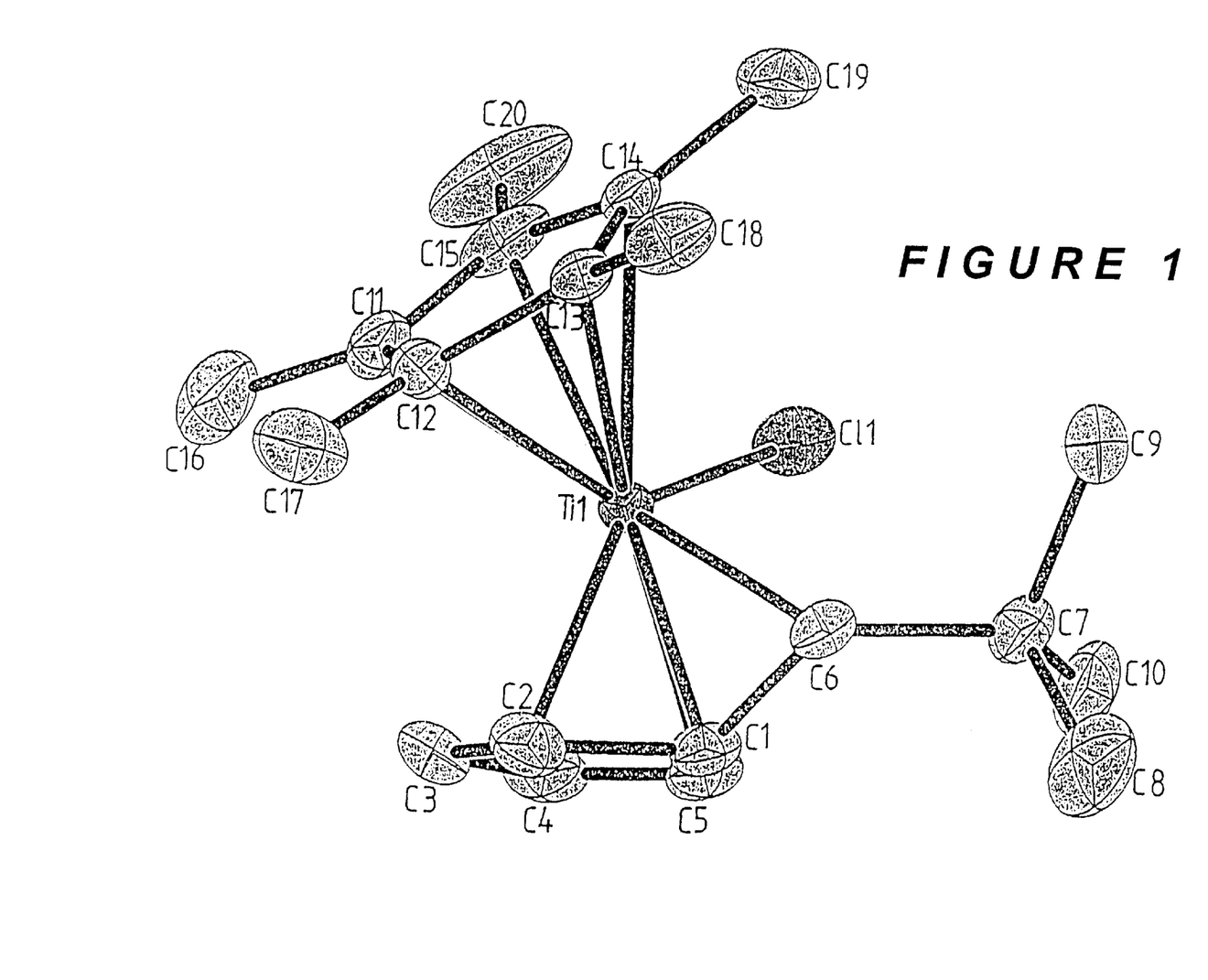
FIG. 1 shows the structure of a fulvene-metal complex according to the present invention.

FIG. 1 shows in perspecitve the structure of a fulvene-metal complex which can be prepared according to the invention such as is obtained by X-ray structure analysis, taking the compound (6-tert-butylfulvenyl) pentamethylcyclopentadienyl)titanium chloride as an example.

The process according to the invention opens up an access to new fulvene-metal complexes of the formula (I) which e.g. cannot be formed by thermolysis.

The present invention therefore also provides fulvene-metal complexes of the formula (I) in which M is a metal from the group consisting of titanium, zirconium, hafnium, vanadium, niobium, tantalum and chromium, k is 1 and A, X, m, p, $R^1$, $R^2$, $R^3$, $R^4$, $R^5$ and $R^6$ have the abovementioned meaning, with the exception of the compounds of the formula (I) wherein $R^1$ and $R^2$ represent hydrogen and at the same time $R^3$, $R^4$, $R^5$ and $R^6$ represent a methyl group and at the same time A denotes a pentamethylcyclopentadienyl group or a carboranediyl group of the formula $C_2B_9 11_{11}$.

The present invention also provides a catalyst system comprising a a) fulvene-metal complex of the formula (I) prepared by the process according to the invention, wherein
M is a metal from the group consisting of titanium, zirconium, hafnium, vanadium, niobium, tantalum and chromium,
k is 1 and
A, X, m, p, $R^1$, $R^2$, $R^3$, $R^4$, $R^5$ and $R^6$ have the abovementioned meaning, and b) a cocatalyst suitable for activating the metal complex a), the molar ratio of component a) to component b) being in the range from 1:0.1 to 1:10,000, preferably 1:1 to 1;1,000.

Possible cocatalysts are the cocatalysts known in the field of metallocene catalysis, such as polymeric or oligomeric aluminoxanes, Lewis acids and aluminates and borates. In this connection, reference is made in particular to Macromol. Symp. Vol. 97, July 1995, p. 1–246 (for alumoxanes) and to EP 277 003, EP 277 004 and Organometallics 1997, 16, 842–857 (for borates), and EP 573 403 (for aluminates).

Particularly suitable cocatalysts are methylaluminoxane, methylalumoxane and diisobutylalumoxane modified by triisobutylaluminium, trialkylaluminium compounds, such as trimethylaluminium, triethylaluminium, triisobutylaluminium and triisooctylaluminium, and furthermore dialkylaluminium compounds, such as diisobutylaluminium hydride, diisobutylaluminium fluoride and diethylaluminium chloride, substituted triarylaluminium compounds, such as tris(pentafluorophenyl)aluminium, and ionic compounds which contain tetrakis(pentafluorophenyl)aluminate as the anion, such as triphenylmethyl tetrakis (pentafluorophenyl)aluminate and N,N-dimethylanilinium tetrakis(pentafluorophenyl)aluminate, substituted triarylboron compounds, such as tris(pentafluorophenyl)boron, and ionic compounds which contain tetrakis(pentafluorophenyl) borate as the anion, such as triphenylmethyl tetrakis (pentafluorophenyl)borate and N,N-dimethylanilinium tetrakis(pentafluorophenyl)borate. Mixtures of various cocatalysts are also suitable for activation of the fulvene-metal complexes of the formula (I).

The present invention also provides the use of the new catalyst system for the polymerization of unsaturated compounds, in particular olefins and dienes. Both homopolymerization and copolymerization of the unsaturated compounds mentioned are understood as polymerization here. Compounds which are employed in particular in the polymerization are $C_2$–$C_{10}$-alkenes, such as ethylene, propylene, but-1-ene, pent-1-ene and hex-1-ene, oct-1-ene and isobutylene, and arylalkenes, such as styrene. Dienes which are employed in particular are: conjugated dienes, such as 1,3-butadiene, isoprene and 1,3-pentadiene, and non-conjugated dienes, such as 1,4-hexadiene, 1,5-heptadiene, 5,7-dimethyl-1,6-octadiene, 4-vinyl-1-cyclohexene, 5-ethylidene-2-norbornene, 5-vinyl-2-norbornene and dicyclopentadiene.

The catalysts according to the invention are suitable for the preparation of rubbers based on copolymers of ethylene with one or more of the α-olefins mentioned and the dienes mentioned. The catalyst system according to the invention is furthermore suitable for the polymerization of cyclo-olefins, such as norbornene, cyclopentene, cyclohexene and cyclooctene, and the copolymerization of cycloolefins with ethylene or α-olefins.

The polymenrization can be carried out in the liquid phase, in the presence or absence of an inert solvent or in the gas phase. Suitable solvents are aromatic hydrocarbons, such as benzene and/or toluene, or aliphatic hydrocarbons, such as propane, hexane, heptane, octane, isobutane or cyclohexane, or mixtures of the various hydrocarbons.

It is possible to employ the catalyst system according to the invention applied to a support. Suitable support materials which may be mentioned are e.g.: inorganic or organic polymeric supports, such as silica gel, zeolites, carbon black, active charcoal, aluminium oxide, polystyrene and polypropylene.

The catalyst system according to the invention can be applied here to the support materials in the conventional manner. Methods of supporting catalyst systems are described, for example, in U.S. Pat. Nos. 4,808,561, 4,912, 075, 5,008,228 and 4,914,253.

The polymerization is in general carried out under pressures of 1 to 1,000, preferably 1 to 100 bar and at temperatures of –100 to +250° C., preferably 0 to +150° C. The polymerization can be carried out continuously or discontinuously in conventional reactors.

The invention is explained in more detail with the aid of the following examples.

General information: Organometallic compounds were prepared and handled with the exclusion of air and moisture under argon protection (Schlenk technique). All the solvents required were rendered absolute before use by boiling over a suitable desiccant for several hours and subsequent distillation under argon. The compounds were characterized by $^1$H-NMR, $^{13}$C-NMR and mass spectroscopy.

Abbreviations

| | |
|---|---|
| Cp | cyclopentadienyl |
| Cp* | pentamethylcyclopentadienyl |
| HV | high vacuum |
| RT | room temperature |
| THF | tetrahydrofuran |
| MS | mass spectrum |
| EA | elemental analysis |
| Tg | glass transition temperature (DSC measurement) |
| de | diastereomer excess |

Synthesis of the Compounds of the Formula (I)

EXAMPLE 1

Fulvene complex synthesis by reaction of 6,6-dimethylfulvene with Cp*TiCl$_3$ in the presence of magnesium [(C$_5$(CH$_3$)$_5$)(C$_5$H$_4$)C(CH$_3$)$_2$TiCl]

Cp*TiCl$_3$ (0.610 g, 2.11 mmol) and 1.05 equivalents of magnesium (0.054 g, 2.21 mmol) were initially introduced into 25 ml THF. 1.05 equivalents of 6,6-dimethylfulvene (0.227 g, 2.14 mmol) were added dropwise to this mixture at room temperature. The mixture was subsequently stirred overnight at RT so that all the Mg was consumed. The solvent was removed under HV and the green residue was taken up in hexane. The solid was filtered off and the solution was concentrated to half, green shiny platelets precipitating out. For recrystallization, the mixture was cooled to –20° C. The olive-green crystals were isolated and dried under HV. 0.429 g (59%) [(C$_5$(CH$_3$)$_5$)(C$_5$H$_4$)C(CH$_3$)$_2$TiCl] was obtained.

$^1$H-NMR:(C$_6$D$_6$, 300 MHz): δ=1.16 (s, 3H, C(C$\underline{H}_3$)$_2$, 1.70 (s, 15 H, C$_5$(C$\underline{H}_3$)$_5$), 1.75 (s, 3H, C(C$\underline{H}_3$)$_2$), 3.43, 4.65, 6.03, 6.70 (m, 1H, C$_5$$\underline{H}_4$) ppm.

$^{13}$C-NMR:(C$_6$D$_6$, 75 MHz): δ=12.82 (C$_5$($\underline{C}$H$_3$)$_5$), 22.76, 24.50 (C($\underline{C}$H$_3$)$_2$), 108.10 ($\underline{C}$(CH$_3$)$_2$) 117.23, 117.46, 120.04, 124.09 ($\underline{C}_4$H$_4$), 122.55 ($\underline{C}_5$($\underline{C}$H$_3$)$_5$), 132.16 (ipso-$\underline{C}_5$H$_4$) ppm.

MS (70 eV) m/e/ (%): 324 (40) [M$^+$], 288 (40) [M$^+$-HCl], 135 (5) [Cp*], 106 (100) [dimethylfulvene].

EXAMPLE 2

Fulvene complex synthesis by reaction of 6,6-dimethylfulvene with Cp*TiCl$_3$ in the presence of butyllithium [(Cp*)(C$_5$H$_4$=C(CH$_3$)$_2$)TiCl]

400 mg (1.38 mmol) Cp*TiCl$_3$, 154 mg (1.45 mmol) 6,6-dimethylfulvene and 1.11 ml (2.76 mmol) n-butyllithium were combined in 25 ml THF in a Schlenk vessel at a temperature of −78° C. The mixture was allowed to warn slowly to 0° C. and was stirred for a further two hours at this temperature in order to bring the reaction to completion. The solvent was then removed under HV and the green residue was taken up in n-hexane. The solid was filtered off and the solution was concentrated to half, green crystals precipitating out. 290 mg (65%) [(C$_5$(CH$_3$)$_5$)(C$_5$H$_4$)C(CH$_3$)$_2$TiCl] were obtained.

$^1$H-NMR: (C$_6$D$_6$, 300 MHz) δ=1.16 (s, 3H, C(CH$_3$)$_2$), 1.70 (s, 15 H, C$_5$(CH$_3$)$_5$), 1.75 (s, 3H, C(CH$_3$)$_2$), 3.43/4.65/6.03/6.70 (s, 1H, C$_5$H$_4$).

$^{13}$C-NMR: (C$_6$D$_6$, 75 MHz) δ=12.82 (C$_5$(CH$_3$)$_5$), 22.76/24.50 (C(CH$_3$)$_2$), 108.10 (C(CH$_3$)$_2$) 117.23/117.46/120.04/124.09 (C$_4$H$_4$), 122.55 (C$_5$(CH$_3$)$_5$), 132.16 (ipso-C).

EXAMPLE 3

Fulvene complex synthesis by reaction of 6,6-dimethylfulvene with Cp*ZrCl$_3$ in the presence of magnesium [(C$_5$(CH$_3$)$_5$)(C$_5$H$_4$)C(CH$_3$)$_2$ZrCl]

Cp*ZrCl$_3$ (0.380 g, 1.14 mmol) and 1.1 equivalents of magnesium (0.031 g, 1.26 mmol) were initially introduced into 10 ml THF. 1.1 equivalents of 6,6-dimethylfulvene (0.134 g, 1.26 mmol) were added dropwise to this solution. After 5 min clouding of the reaction solution occurred. The mixture was stirred overnight so that the magnesium dissolved completely. It was concentrated to dryness under HV, the residue was taken up in 10 ml hexane and the precipitate formed was filtered off. 197 mg (47%) [(C$_5$(CH$_3$)$_5$)(C$_5$H$_4$)C(CH$_3$)$_2$ZrCl] were isolated from the filtrate brown-red solid.

$^1$H-NMR:(C$_6$D$_6$, 300 MHz): δ=1.77 (s, 15H, C$_5$(CH$_3$)$_5$), 1.98, 1.99 (s, 3H, C(CH$_3$)$_2$), 5.40 (dd, 1H, $^3$J(H,H)=2.69, 3.02 Hz, C$_5$H$_4$), 5.58 (dd, 1H, $^3$J(H,H)=2.69, 2.68 Hz, C$_5$H$_4$), 5.85 (dd, 1H, $^3$J(H,H)=2.68, 3.02 Hz, C$_5$H$_4$), 5.92 (dd, 1H, $^3$J=2.69, 2.68 Hz, C$_5$H$_4$) ppm.

$^{13}$C-NMR:(C$_6$D$_6$, 75 MHz): δ=10.98 (C$_5$(CH$_3$)$_5$), 21.35, 21.90 (C(CH$_3$)$_2$, 109.78 (C(CH$_3$)$_2$), 107.75, 110.68, 113.88, 118.11 (C$_5$H$_4$), 115.69 (ipso-C$_5$H$_4$), 122.35 (C(CH$_3$)$_5$) ppm.

MS (70 eV) m/e (%): 366 (10) [M$^+$], 330 (5) [M$^+$-HCl], 259 (2), 135 (5) [Cp*], 106 (100) [dimethylfulvene].

EXAMPLE 4

Synthesis of bis(η$^6$-6,6-diphenylfulvene)titanium by reaction of 6,6-diphenylfulvene with titanium tetrachloride in the presence of magnesium 610 mg (1.83 mmol) TiCl$_4$(THF)$_2$, 89 mg (3.65 mmol) magnesium filings and 841 mg (3.65 mmol) 6,6-diphenylfulvene were combined in 30 ml THF as the reaction medium in a Schlenk vessel. The mixture was stirred for 12 h, until the magnesium filings had been consumed completely, in order to bring the reaction to completion. By concentrating the reaction solution to dryness a green solid was obtained, which could be separated off from the magnesium chloride formed by taking up in n-hexane and filtration. 640 mg (70%) bis(η$^6$-6,6-diphenylfulvene) titanium were obtained by stepwise concentration and cooling of the filtrate.

EXAMPLE 5

Fulvene complex synthesis by reaction of 6,6-dimethylfulvene with CpTiCl$_3$ in the presence of magnesium [(C$_5$H$_5$)(C$_5$H$_4$)C(CH$_3$)$_2$TiCl]

CpTiCl$_3$ (0.410 g, 1.87 mmol) and 1.05 equivalents of magnesium (0.048 g, 1.96 mmol) were initially introduced into 20 ml THF. 1.03 equivalents of 6,6-dimethylfulvene (0.204 g, 1.92 mmol) were added dropwise to this yellow solution at RT and the mixture was stirred until the magnesium employed had been consumed. It was then concentrated under HV and the resulting green solid was taken up in 20 ml hexane. After the solid had been filtered off, the dark green solution was concentrated to half under HV. 0.2 g (42%) [(C$_5$H$_5$(C$_5$H$_4$)C(CH$_3$)$_2$TiCl] was obtained as a dark green solid by crystallization at −20° C.

$^1$H-NMR:(C$_6$D$_6$, 300 MHz): δ=0.94, 1.64 (s, 3H, C(CH$_3$)$_2$), 3.66 (m, 1H, C$_5$H$_4$), 4.76 (m, 1H, C$_5$H$_4$), 5.80 s, 5H, C$_5$H$_5$), 6.23 (m, 1H, C$_5$H$_4$), 6.66 (m, 1H, C$_5$H$_4$) ppm $^{13}$C-NMR:(C$_6$D$_6$, 75 MHz): δ=10.98 (C$_5$(CH$_3$)$_5$), 21.35, 21.90 (C(CH$_3$)$_2$), 109.78 (C(CH$_3$)$_2$), 107.75, 110.68, 113.88, 118.11 (C$_5$H$_4$), 115.69 (ipso-C$_5$H$_4$), 122.35 (C$_5$(CH$_3$)$_5$) ppm.

EXAMPLE 6

Fulvene complex synthesis by reaction of 6,6-diphenylfulvene with Cp*TiCl$_3$ in the presence of magnesium [(C$_5$(CH$_3$)$_5$)(C$_5$H$_4$)C(C$_6$H$_5$)$_2$TiCl]

Cp*TiCl$_3$ (0.690 g, 2.38 mmol) and 1.1 equivalents of magnesium (0.064 g, 2.62 mmol) were initially introduced into 20 ml THF. 1.1 equivalents of 6,6-diphenylfulvene (0.604 g, 2.62 mmol) were added dropwise to this solution at RT. The mixture was stirred overnight at RT, so that all the magnesium was consumed. The solvent was removed under HV and the green residue was taken up in hexane. The precipitate was filtered off and the solution was concentrated to half. The mixture was cooled to −20° C. for crystallization, 0.29 g (27%) [(C$_5$(CH$_3$)$_5$)(C$_5$H$_4$)C(C$_6$H$_5$)$_2$TiCl] being obtained as a green solid.

$^1$H-NMR:(C$_6$D$_6$), 300 MHz): δ=1.55 (s, 15 H, C$_5$(CH$_3$)$_5$), 4.20, 4.55, 5.89, 6.37 (m, 1H, C$_5$H$_4$), 6.89–7.41 (m, 10H, C$_6$H$_5$) ppm.

$^{13}$C-NMR:(C$_6$D$_6$, 175 MHz): δ=12.38 (C$_5$(CH$_3$)$_5$), 116.29, 117.24, 118.22, 121.82 (C$_4$H$_4$), 124.04 (C$_5$(CH$_3$)$_5$), 125.61 (ipso-C$_5$H$_4$), 126.50, 126.84, 127.26, 128.07, 128.83, 129.81 (C$_6$H$_5$), 130.72 (-C(C$_6$H$_5$)), 141.93, 144.23 (ipso-C$_6$H$_5$) ppm.

MS (70 eV) m/e (%): 448 (5) [M$^{+1}$ 413 (2) [M$^+$-HCl], 230 (100) [6,6-diphenylfulvene], 135 (15) [Cp*], 78 (12) [Ph].

EXAMPLE 7

Fulvene complex synthesis by reaction of 6,6-diphenylfulvene with Cp*ZrCl$_3$ in the presence of magnesium [(C$_5$(CH$_3$)$_5$)(C$_5$H$_4$)C(C$_6$H$_5$)$_2$ZrCl]

Cp*ZrCl$_3$ (0.310 g, 0.93 mmol) and 1.05 equivalents of magnesium (0.024 g, 0.98 mmol) were initially introduced into 10 ml TBF. 1.05 equivalents of 6,6-diphenylfulvene (0.225 g, 0.98 mmol) were added dropwise to this solution. The mixture was stirred overnight, so that the magnesium had reacted completely. It was concentrated to dryness under HV, the residue was taken up in 20 ml toluene and the insoluble precipitate was filtered off. After covering with a layer of hexane at −20° C., 178 mg (39%) [($C_5(CH_3)_5$)($C_5H_4$)C($C_6H_5$)$_2$ZrCl] were obtained as a red solid.

$^1$H-NMR:($C_6D_6$, 300 MHz): δ=1.63 (s, 15 H, $C_5(C\underline{H}_3)_5$), 4.65, 5.20, 5.22, 6.06 (m, 1H, $C_5\underline{H}_4$), 6.98–7.16 (m, 8H, $C_6H_5$), 7.26–7.49 (m, 2H, $C_6H_5$) ppm.

$^{13}$C-NMR:($C_6D_6$, 75 MHz): δ=11.66 ($C_5(\underline{C}H_3)5$), 104.67, 111.14, 113.62, 117.52 ($\underline{C}_4H_4$), 120.82 ($C_5(\underline{C}H_3)_5$), 125.61 (ipso-$\underline{C}_5H_4$), 126.50, 126.84, 127.26, 128.07, 128.83, 129.81 ($\underline{C}_6H_5$), 130.72 (-$\underline{C}(C_6H_5)$), 141.93, 144.23 (ipso-$\underline{C}_6H_5$) ppm.

MS (70 eV) m/e (%): 448 (5) [M$^+$], 413 (2) [M$^+$-HCl], 230 (100) [6,6-diphenylfulvene], 135 (15) [Cp*], 78 (12) [Ph].

EXAMPLE 8

Fulvene complex synthesis by reaction of 2,3,4,5-tetramethylfulvene with Cp*TiCl$_3$ in the presence of magnesium [($C_5(CH_3)_5$)($C_5(CH_3)_4$)CH$_2$TiCl]

Cp*TiCl$_3$ (0.370 g, 1.28 mmol) and 1.05 equivalents of magnesium (0.033 g, 1.35 mmol) were initially introduced into 25 ml THF. 1.05 equivalents 2,3,4,5-tetramethylfulvene (0.185 g, 1.35 mmol) were added dropwise to this red solution at room temperature. The mixture was stirred overnight at RT so that all the magnesium was consumed. The solvent was removed under HV and the green residue was taken up in hexane. The solid was filtered off and the solution was concentrated to half. The mixture was cooled to −20° C. for crystallization, 0.23 g (52%) [($C_5(CH_3)5$)($C_5(CH_3)_4$)CH$_2$TiCl] being obtained as a green solid.

$^1$H-NMR:($C_6D_6$, 300 MHz): δ=1.21, 1.47, 1.70 (s, 3 H, $C_5(C\underline{H}_3)_4$=CH$_2$), 1.79 (s, 3 H, $C_5(C\underline{H}_3)_5$), 2.07 (s, 3 H, $C_5(C\underline{H}_3)_4$=CH$_2$), 1.43 (d, 1H, $^2$J(H,H)=3.66 Hz, $C_5(CH_3)_4$=C$\underline{H}$H), 2.54 (d, 1H, $^2$J(H,H)=3.66 Hz, $C_5(CH_3)_4$=CH$\underline{H}$) ppm.

$^{13}$C-NMR:($C_6D_6$, 75 MHz): δ=9.82, 10.22 ($C_5(\underline{C}H_3)_4$=CH$_2$), 11.13 ($C_5(\underline{C}H_3)_5$), 11.85, 14.00 ($C_5(\underline{C}H_3)_4$=CH$_2$, 77.65 ($C_5(CH_3)_4$=$\underline{C}$H$_2$), 120.08 ($\underline{C}_5(CH_3)_5$, 120.32, 124.43, 124.73, 128.61, 135.17 ($\underline{C}_5(CH_3)_4$=CH$_2$) ppm.

EXAMPLE 9

Fulvene complex synthesis by reaction of 2,3,4,5-tetramethylfulvene with CpTiCl$_3$ in the presence of magnesium [($C_5H_5$)$C_5(CH_3)_4$)CH$_2$TiCl]

CpTiCl$_3$ (0.350 g, 1.60 mmol) and 1.05 equivalents of magnesium (0.041 g, 1.67 mmol) were initially introduced into 20 ml THF. 1.1 equivalents of 2,3,4,5-tetramethylfulvene (0.260 g, 1.67 mmol) were added dropwise to this solution at room temperature and the mixture was stirred until the magnesium employed had been consumed. It was then concentrated under HV and the resulting green solid was taken up in 20 ml hexane. After the solid had been filtered off, the dark green solution was concentrated to half under HV. 0.3 g (67%) [($C_5H_5$)($C_5(CH_3)_4$)CH$_2$TiCl] was obtained as a dark green solid by crystallization at −20° C.

$^1$H-NMR:($C_6D_6$, 300 MHz): δ=0.82, 1.27, 1.74 (s, 3 H, $C_5(C\underline{H}_3)_4$=CH$_2$), 1.99 (d, 1H, $^2$J(H,H)=3.7 Hz, $C_5(CH_3)_4$)=C$\underline{H}$H), 2.05 (s, 3 H, $C_5(C\underline{H}_3)_4$=CH$_2$), 2.56 (d, 1H, $^2$J(H,H)=3.7 Hz, $C_5(CH_3)_4$=CH$\underline{H}$), 5.77 (s, 5H, $C_5\underline{H}_5$) ppm.

$^{13}$C-NMR:($C_6D_6$, 75 MHz): δ=9.47, 10.35, 12.01, 12.95 ($C_5(\underline{C}H_3)_4$=CH$_2$), 74.47 ($C_5(C\underline{H}_3)_4$=CH$_2$), 110.80 ($\underline{C}_5H_5$), 119.92, 124.60, 127.82, 129.43, 134.80 ($\underline{C}_5(CH_3)_4$=CH$_2$) ppm.

MS (70 eV) m/e (%): 283 (10) [M$^{+,}$ 247 (15) [M$^+$-HCl], 134 (50) [2,3,4,5-tetramethylfulvene], 119 (100) [2,3,4,5-tetramethylfulvene-CH$_4$], 65 (30) [Cp].

EXAMPLE 10

Fulvene complex synthesis by reaction of 1,2,3,4,6-pentamethylfulvene with CpTiCl$_3$ in the presence of magnesium [($C_5H_5$)($C_5(CH_3)_4$C(H)(CH$_3$)TiCl]

CpTiCl$_3$ (0.450 g, 2.05 mmol) and 1.05 equivalents of magnesium (0.054 g, 2.15 mmol) were initially introduced into 20 ml THF. 1.03 equivalents of 1,2,3,4,6-pentamethylfulvene (0.320 g, 2.15 mmol) were added dropwise to this solution at RT and the mixture was stirred until the magnesium employed had been consumed. It was then concentrated under HV and the resulting green solid was taken up in 20 ml hexane. After the solid had been filtered off, the dark green solution was concentrated to half under HV. 0.17 g (28%) [($C_5H_5$)($C_5(CH_3)_4$)C(H)(CH$_3$)TiCl] was obtained as a dark green solid by crystallization at −20° C.

de: 25%

$^1$H-NMR:($C_6D_6$, 300 MHz): δ=0.73, 1.12 (s, 3 H, $C_5(C\underline{H}_3)_4$=C(CH$_3$)(H)), 1.64 (d, 3H, $^3$J(H,H)=7.25 Hz, $C_5(CH_3)_4$=C(C$\underline{H}_3$)(H)), 1.71 (s, 3 H, $C_5(C\underline{H}_3)_4$=C(CH$_3$)(H)), 2.29 (q, 1H, $^3$J(H,H)=7.25 Hz, $C_5(CH_3)_4$=C(CH$_3$)($\underline{H}$)), 2.55 (s, 3 H, $C_5(C\underline{H}_3)_4$=C(CH$_3$)(H)), 5.79 (s, 5H, $C_5\underline{H}_5$) ppm.

$^{13}$C-NMR:($C_6D_6$, 75 MHz): δ=10.87, 13.35, 16.19, 16,97 ($C_5(\underline{C}H_3)_4$=C(CH$_3$)(H)), 37.62 ($C_5(CH_3)_4$=C($\underline{C}H_3$)(H)), 94.39 ($C_5(CH_3)_4$)=$\underline{C}$(CH$_3$)(H)), 112.02 ($\underline{C}_5H_5$), 121.46, 125.56, 130.91, 131.46, 136.90 ($C_5(\underline{C}H_3)_4$=C(CH$_3$)(H)) ppm.

EXAMPLE 11

Fulvene complex synthesis by reaction of 6-tert-butylfulvene with Cp*TiCl$_3$ in the presence of magnesium [($C_5(CH_3)_5$)($C_5H_4$)C(H)(C(CH$_3$)$_3$)TiCl]

Cp*TiCl$_3$ (0.450 g, 1.55 mmol) and 1.05 equivalents of magnesium (0.039 g, 1.63 mmol) were initially introduced into 15 ml THF. 1.05 equivalents of tert-butylfulvene (0.249 g, 1.61 mmol) were added dropwise to this solution at RT. The mixture was stirred overnight at RT so that all the magnesium was consumed. The solvent was removed under HV and the green residue was taken up in hexane. The solid was filtered off and the solution was concentrated to half. The mixture was cooled to −20° C. for crystallization, 0.35g (64%) [($C_5(CH_3)_5$)($C_5H_4$)C(H)-(C(CH$_3$)$_3$)TiCl] being obtained as green crystals.

An X-ray structure analysis was carried out (FIG. 1).

de: ≧98%

$^1$H-NMR:($C_6D_6$, 300 MHz): δ=1.16 (s, 9H, $C_5H_4$=C(H)(C(C$\underline{H}_3$)$_3$)), 1.68 (s, 1 H, $C_5H_4$=C($\underline{H}$)(C(CH$_3$)$_3$)), 1.70 (s, 15H, $C_5(C\underline{H}_3)_5$), 3.15, 4.74, 5.97, 6.63 (m, 1H, $C_5\underline{H}_4$=C(H)(C(CH$_3$)$_3$)) ppm.

$^{13}$C-NMR:($C_6D_6$, 75 MHz): δ=11.69 ($C_5(\underline{C}H_3)_5$), 32.30 ($C_5H_4$=C(H)(C($\underline{C}H_3$)$_3$)), 34.28 ($C_5H_4$=C(H)($\underline{C}$(CH$_3$)$_3$)), 114.31 ($C_5H_4$=$\underline{C}$(H)(C(CH$_3$)$_3$)), 117.83, 118.31, 118.77 ($\underline{C}_5H_4$=C(H)(C(CH$_3$)$_3$)), 120.46 ($\underline{C}_5(CH_3)_5$), 124.72, 128.23 ($C_5H_4$=C(H)(C(CH$_3$)$_3$)) ppm.

MS (70 eV) m/e (%): 353 (12) [M⁺], 316 (5) [M⁺-HCl], 270 (18), 235 (8), 135 (100) [Cp*], 119 (35), 80 (85), 57 (90) [C(CH₃)₃].

EXAMPLE 12

Fulvene complex synthesis by reaction of 6-tert-butylfulvene with CpTiCl₃ in the presence of magnesium [(C₅H₅)(C₅H₄)C(H)(C(CH₃)₃)TiCl]

CpTiCl₃ (0.420 g, 1.91 mmol) and 1.05 equivalents of magnesium (0.048 g, 2.01 mmol) were initially introduced into 10 ml THF. 1.03 equivalents of tert-butylfulvene (0.295 g, 1.91 mmol) were added dropwise to this solution at RT and the mixture was stirred under the magnesium employed was consumed. It was then concentrated under HV and the resulting green solid was taken up in 20 ml hexane. After the solid had been filtered off, the dark green solution was concentrated to half under HV. 0.23 g (44%) [(C₅H₅)(C₅H₄)C(H)(C(CH₃)₃)TiCl] was obtained as dark green crystals by crystallization at −20° C.

de: ≧98%

¹H-NMR:(C₆D₆, 300 MHz): δ=1.05 (s, 9H, C₅H₄=C(H)(C(C$\underline{H}$₃)₅)), 2.05 (s, 1 H, C₅H₄=C($\underline{H}$)(C(CH₃)₃)), 3.28, 4.83 (m, 1H, C₅$\underline{H}$₄=C(H)(C(CH₃)₃)),) 5,85 (s, 5H, C₅$\underline{H}$₅), 6.17, 6.59 (m, 1H, C₅$\underline{H}$₄=C(H)(C(CH₃)₃)) ppm.

¹³C-NMR:(C₆D₆, 75 MHz): δ=32.84 (C₅H₄=C(H)(C($\underline{C}$H₃)₃)), 35.76 (C₅H₄=C(H)($\underline{C}$(CH₃)₃)), 111.23 ($\underline{C}$₅H₅), 111.63 (C₅H₄=$\underline{C}$(H)(C(CH₃)₃)), 116.62, 117.41, 121.63, 127.65, 127.50 ($\underline{C}$₅H₄=C(H)(C(CH₃)₃)) ppm.

MS (70 eV) m/e (%): 282 (5) [M⁺], 246 (45) [M⁺-HCl], 228 (15), 135 (10) [Cp*], 119 (35).

Polymerization Examples

EXAMPLE 13
Preparation of the Catalyst Solution 8.3 mg (22.6 μmol) [(Cp*)(C₅H₄=C(CH₃)₂)ZrCl] from example 3 were dissolved in 11.3 ml toluene.
Polymerization of Ethylene 100 ml toluene were initially introduced into a 250 ml glass reactor and 1 ml of a 0.1 molar solution of triisobutylaluminium in toluene and 0.5 ml of the catalyst solution were added. Ethylene was then passed continuously into the solution under a pressure of 1.1 bar with a gas inlet tube. The polymerization was initiated by addition of 1 ml of a 0.001 molar solution of N,N-dimethylanilinium tetrakis (pentafluorophenyl)borate in toluene. After a polymerization time of 5 min at a temperature of 40° C. under an ethylene pressure of 1.1 bar, the reaction was stopped by addition of 10 ml methanol and the polymer formed was filtered off, washed with acetone and dried in a vacuum drying cabinet. 1.61 g polyethylene were obtained.

EXAMPLE 14
Copolymerization of Ethylene and Propylene 500 ml toluene and 5 ml of a 10% MAO solution in toluene were initially introduced into a 1.4l steel autoclave, equipped with a mechanical stirrer, manometer, temperature probe, temperature control device, catalyst sluice and monomer metering devices for ethylene and propylene, and were stirred for 10 min. 52 g propylene were then metered in. The internal temperature was adjusted to 40° C. with a thermostat. Ethylene was then metered in until the internal pressure in the reactor rose to 6 bar. The polymerization was initiated by addition of 5 ml of the catalyst solution from example 5 and ethylene was metered in continuously such that the internal pressure at 40° C. was constant at 6 bar. After a polymerization time of 1 hour the polymerization was stopped with a 1% HCl solution in methanol, the mixture was stirred for 10 min and the polymer was then precipitated in methanol. The polymer thus obtained was washed with methanol, isolated and dried in vacuo at 60° C. for 20 h, 48 g copolymer being obtained. Determination of the composition of the copolymer by IR spectroscopy showed an incorporation of 82.9% ethylene and 17.1% propylene. A Tg of −24° C. was determined by the DSC method.

EXAMPLE 15
Preparation of the Catalyst 73.9 mg (0.221 mmol) TiCl₄(THF)₂ were dissolved in 3 ml THF. 5.4 mg (0.22 mmol) magnesium and 51 mg (0.221 mmol) 6,6-diphenylfulvene were then added. After stirring at 20° C. for 20 h, a dark green solution was obtained. The solution was concentrated to dryness, the residue formed was dried under HV for 2 h and 22 ml toluene were then added, a dark green suspension being formed. 1 ml of the catalyst suspension contained 0.01 mmol titanium.
Polymerization of Ethylene

90 ml toluene and 5 ml of an MAO solution (10% in toluene) were initially introduced into a 250 ml glass reactor and were stirred for 5 minutes. 5 ml of the catalyst suspension were then added and the mixture was stirred at 40° C. for 10 minutes. Ethylene was then passed continuously into the solution with a gas inlet tube. After a polymerization time of 10 min at a temperature of 40° C. and an ethylene pressure of 1.1 bar, the reaction was stopped by addition of 10 ml of a 1% solution of HCl in methanol and the polymer formed was filtered off, washed with methanol and dried in a vacuum drying cabinet. 8.9 g polyethylene were obtained.

What is claimed is:

1. Process for the preparation of fulvene-metal complexes of the formula (Ia)

or of the formula (Ib)

wherein
    M is a metal from group IIIb, IVb, Vb or VIb or the lanthanides or the actinides of the periodic table of the elements according to IUPAC,
    A denotes an anionic ligand optionally with one or more bridges,
    X denotes a hydrogen atom, a C₁- to C₁₀-alkyl group, a C₁- to C₁₀-alkoxy group, a C₆- to C₁₀-aryl group, a C₆- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a silyl group substituted by $C_1$- to $C_{10}$-hydrocarbon radicals, a halogen atom or an amide of the formula $NR^7{}_2$, L denotes a neutral ligand, $R^1$, $R^2$, $R^3$, $R^4$, $R^5$, and $R^6$ are identical or different and represent hydrogen, halogen, a cyano group, a $C_1$- to $C_{20}$-alkyl group, a $C_1$- to $C_{10}$-fluoroalkyl group, a $C_6$- to $C_{10}$-fluoroaryl group, a $C_1$- to $C_{10}$-alkoxy group, a $C_6$- to $C_{20}$-aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a $C_2$- to $C_{10}$-alkenyl group, a silyl group substituted by $C_1$–$C_{10}$-hydrocarbon radicals, a sulfide group substituted by a $C_1$–$C_{10}$-hydrocarbon radical or an amino group which is optionally substituted by $C_1$–$C_{20}$-hydrocarbon radicals, or $R^1$, $R^2$, $R^3$, $R^4$, $R^5$, and $R^6$, in each case together with the atoms connecting them, form one or more aliphatic or aromatic ring systems, which optionally contain one or more heteroatoms (O, N, S) and 5 to 10 carbon atoms, $R^7$ represents hydrogen, a $C_1$- to $C_{20}$-alkyl group, a $C_6$- to $C_{20}$-aryl group, a $C_7$- to $C_{40}$-arylalkyl group, a $C_7$- to $C_{40}$-alkylaryl group, a silyl group substituted by $C_1$–$C_{10}$-hydrocarbon radicals or an amino group which is optionally substituted by $C_1$–$C_{20}$-hydrocarbon radicals, m, p represent the numbers 0, 1, 2, 3 or 4, which result from the valency and the bonding state of M, and k represents the number 1, 2 or 3, and the sum of k+m+p is 1 to 5, depending on the oxidation level of M, and n is a number from 0 to 10, by reaction of a transition metal compound of the formula (IIa) or (IIb)

or wherein

A, X, L, M, m, and n have the abovementioned meaning and s is 2, 3, 4, 5 or 6 an s is >p, with a fulvene compound of the formula (III)

wherein $R^1$, $R^2$, $R^3$, $R^4$, $R^5$ and $R^6$ have the abovementioned meaning, in the presence of a reducing agent.

2. Process according to claim 1, characterized in that the reaction is carried out in a suitable reaction medium at temperatures of −100 to +250° C.

3. Process according to claim 1, characterized in that alkali metals, alkaline earth metals or lithium-alkyls are used as the reducing agent.

4. Process according to claim 1, characterized in that the reaction is carried out in a solvent.

5. Process according to claim 4, characterized in that the reaction is carried out in an ether.

6. Fulvene-metal complexes comprising the formula (Ia)

or of the formula (Ib)

wherein

A denotes an anionic ligand optionally with one or more bridges, with the exception of cyclopentadienyl ligands X denotes a hydrogen atom, a $C_1$- to $C_{10}$-alkyl group, a $C_1$- to $C_{10}$-alkoxy group, a $C_6$- to $C_{10}$-aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a silyl group substituted by $C_1$- to $C_{10}$-hydrocarbon radicals, a halogen atom or an amide of the formula $NR^7{}_2$, L denotes a neutral ligand, $R^1$, $R^2$, $R^3$, $R^4$, $R^5$, and $R^6$ are identical or different and represent hydrogen, halogen, a cyano group, a $C_1$- to $C_{20}$-alkyl group, a $C_1$- to $C_{10}$-fluoroalkyl group, a $C_6$- to $C_{10}$-fluoroaryl group, a $C_1$- to $C_{10}$-alkoxy group, a $C_6$- to $C_{20}$- aryl group, a $C_6$- to $C_{10}$-aryloxy group, $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a $C_2$- to $C_{10}$-alkenyl group, a silyl group substituted by $C_1$-$C_{10}$-hydrocarbon radicals, a sulfide group substituted by a $C_1$–$C_{10}$-hydrocarbon radical or an amino group which is optionally substituted by $C_1$–$C_{20}$-hydrocarbon radicals, or $R^1$, $R^2$, $R^3$, $R^4$, $R^5$, and $R^6$, in each case together with the atoms connecting them, form one or more aliphatic or aromatic ring systems, which can contain one or more heteroatoms (O, N, S) and 5 to 10 carbon atoms, $R^7$ represents hydrogen, a $C_1$- to $C_{20}$-alkyl group, a $C_6$- to $C_{20}$-aryl group, a $C_7$- to $C_{40}$-arylalkyl group, a $C_7$- to $C_{40}$-alkylaryl group, a silyl group substituted by $C_1$–$C_{10}$-hydrocarbon radicals or an amino group which is optionally substituted by $C_1$–$C_{20}$-hydrocarbon radicals, m, p represent the numbers 0, 1, 2, 3 or 4, which result from the valency and the bonding state of M, and n is a number from 0 to 10,

M is a metal from the group consisting of titanium, zirconium, hafnium, vanadium, niobium, tantalum and chromium, k is 1; with the exception of the compounds of the formula (Ia) or (Ib) wherein $R^1$ and $R^2$ represent hydrogen and at the same time $R^3$, $R^4$, $R^5$ and $R^6$ represent a methyl group and at the same time A denotes a pentamethylcyclopentadienyl group or a carboranediyl group of the formula $C_2B_911_{11}$.

7. A catalyst system comprising:

a) a fulvene metal complex of the formula (Ia)

(Ia)

or of the formula (Ib)

(Ib)

wherein

A denotes an anionic ligand optionally with one or more bridges,

X denotes a hydrogen atom, a $C_1$- to $C_{10}$-alkyl group, a $C_1$- to $C_{10}$-alkoxy group, a $C_6$- to $C_{10}$-aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a silyl group substituted by $C_1$- to $C_{10}$-hydrocarbon radicals, a halogen atom or an amide of the formula $NR^7_2$, L denotes a neutral ligand, $R^1$, $R^2$, $R^3$, $R^4$, $R^5$, and $R^6$ are identical or different and represent hydrogen, halogen, a cyano group, a $C_1$- to $C_{20}$-alkyl group, a $C_1$- to $C_{10}$-fluoroalkyl group, a $C_6$- to $C_{10}$-fluoroaryl group, a $C_1$- to $C_{10}$-alkoxy group, a $C_6$- to $C_{20}$- aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a $C_2$- to $C_{10}$-alkenyl group, a silyl group substituted by $C_1$–$C_{10}$-hydrocarbon radicals, a sulfide group substituted by a $C_1$–$C_{10}$-hydrocarbon radical or an amino group which is optionally substituted by $C_1$–$C_{20}$-hydrocarbon radicals, or $R^1$, $R^2$, $R^3$, $R^4$, $R^5$, and $R^6$, in each case together with the atoms connecting them, form one or more aliphatic or aromatic ring systems, which can contain one or more heteroatoms (O, N, S) and 5 to 10 carbon atoms, $R^7$ represents hydrogen, a $C_1$- to $C_{20}$-alkyl group, a $C_6$- to $C_{20}$-aryl group, a $C_7$- to $C_{40}$-arylalkyl group, a $C_7$- to $C_{40}$-alkylaryl group, a silyl group substituted by $C_1$–$C_{10}$-hydrocarbon radicals or an amino group which is optionally substituted by $C_1$–$C_{20}$-hydrocarbon radicals, m, p represent the numbers 0, 1, 2, 3 or 4, which result from the valency and the bonding state of M, and n is a number from 0 to 10, wherein M is a metal from the group consisting of titanium, zirconium, hafnium, vanadium, niobium, tantalum and chromium, K is 1 and b) a cocatalyst suitable for activating the metal complex a), the molar ratio of component a) to component b) being in the range from 1:0.1 to 1:10,000.

8. The polymerization of olefins and/or dienes comprising a catalyst system a) a fulvene metal complex of the formula (Ia)

(Ia)

or of the formula (Ib)

(Ib)

wherein

A denotes an anionic ligand optionally with one or more bridges,

X denotes a hydrogen atom, a $C_1$- to $C_{10}$-alkyl group, a $C_1$- to $C_{10}$-alkoxy group, a $C_6$- to $C_{10}$-aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a silyl group substituted by $C_1$- to $C_{10}$-hydrocarbon radicals, a halogen atom or an amide of the formula $NR^7_2$, L denotes a neutral ligand, $R^1$, $R^2$, $R^3$, $R^4$, $R^5$, and $R^6$ are identical or different and represent hydrogen, halogen, a cyano group, a $C_1$- to $C_{20}$-alkyl group, a $C_1$- to $C_{10}$-fluoroalkyl group, a $C_6$- to $C_{10}$-fluoroaryl group, a $C_1$- to $C_{10}$-alkoxy group, a $C_6$- to $C_{20}$- aryl group, a $C_6$- to $C_{10}$-aryloxy group, a $C_2$- to $C_{10}$-alkenyl group, a $C_7$- to $C_{40}$-arylalkyl group, a $C_7$- to $C_{40}$-alkylaryl group, a $C_8$- to $C_{40}$-arylalkenyl group, a $C_2$- to $C_{10}$-alkenyl group, a silyl group substituted by $C_1$–$C_{10}$-hydrocarbon radicals, a sulfide group substituted by a $C_1$–$C_{10}$-hydrocarbon radical or an amino group which is optionally substituted by $C_1$–$C_{20}$-hydrocarbon radicals, or $R^1$, $R^2$, $R^3$, $R^4$, $R^5$, and $R^6$, in each case together with the atoms connecting them, form one or more aliphatic or aromatic ring systems, which can contain one or more heteroatoms (O, N, S) and 5 to 10 carbon atoms, $R^7$ represents hydrogen, a $C_1$- to $C_{20}$-alkyl group, a $C_6$- to $C_{20}$-aryl group, a $C_7$- to $C_{40}$-arylalkyl group, a $C_7$- to $C_{40}$-alkylaryl group, a silyl group substituted by $C_1$–$C_{10}$-hydrocarbon radicals or an amino group which is optionally substituted by $C_1$–$C_{20}$-hydrocarbon radicals, m, p represent the numbers 0, 1, 2, 3 or 4, which result from the valency and the bonding state of M, and n is a number from 0 to 10, wherein M is a metal from the group consisting of titanium, zirconium, hafnium, vanadium, niobium, tantalum and chromium, K is 1 and b) a cocatalyst suitable for activating the metal complex a), the molar ratio of component a) to component b) being in the range from 1:0.1 to 1:10,000.

* * * * *